United States Patent [19]

Romano et al.

[11] 4,218,391

[45] Aug. 19, 1980

[54] METHOD FOR THE PREPARATION OF ESTERS OF CARBONIC ACID

[75] Inventors: Ugo Romano; Renato Tesei; Gioacchino Cipriani; Lidio Micucci, all of Milan, Italy

[73] Assignee: Anic, S.p.A., Italy

[21] Appl. No.: 17,332

[22] Filed: Mar. 5, 1979

Related U.S. Application Data

[63] Continuation of Ser. No. 832,628, Sep. 12, 1977, abandoned.

[30] Foreign Application Priority Data

Sep. 30, 1976 [IT] Italy ................. 27825 A/76

[51] Int. Cl.$^2$ ............................ C07C 68/00
[52] U.S. Cl. .................................. 260/463
[58] Field of Search ............................ 260/463

[56] References Cited

U.S. PATENT DOCUMENTS

| | | | |
|---|---|---|---|
| 3,114,762 | 12/1963 | Mador et al. | 260/463 |
| 3,227,740 | 1/1966 | Fenton | 260/463 |
| 3,845,468 | 11/1974 | Perrotti et al. | 260/463 |
| 3,980,690 | 9/1976 | Cipriani et al. | 260/463 |

FOREIGN PATENT DOCUMENTS

| | | | |
|---|---|---|---|
| 2110194 | 3/1976 | Fed. Rep. of Germany | 260/463 |
| 45-11129 | 4/1970 | Japan | 260/463 |
| 45-24966 | 8/1970 | Japan | 260/463 |

OTHER PUBLICATIONS

B. K. Nefedov et al., Chem. Abstracts, 79: 41858k, (1973).

*Primary Examiner*—Donald G. Daus
*Assistant Examiner*—M. C. Eakin
*Attorney, Agent, or Firm*—Morgan, Finnegan, Pine, Foley & Lee

[57] ABSTRACT

Carbonic acid esters are prepared by reacting the alcohol concerned with oxygen and carbon monoxide in the presence of a catalyst which is a salt of a metal belonging to the Groups IB, IIB and VIII of the Periodic Table: the least possible number of inorganic anions is desirable in order to reduce the acidity of the environment as far as possible. The salts of monovalent copper are preferred and high yields and selectivities are obtained.

7 Claims, No Drawings

METHOD FOR THE PREPARATION OF ESTERS OF CARBONIC ACID

This is a continuation, of application Ser. No. 832,628 filed Sept. 12, 1977 now abandoned.

This invention relates to a method for the preparation of esters of carbonic acid, such method comprising the step of reacting the alcohol, which is intended to be esterified, with carbon monoxide and oxygen in the presence of a catalyst composed by a metal salt, preferably a copper salt, with its metallic ion bound to the least possible number of inorganic anions.

Esters of carbonic acid are known in the art: they find a use as solvents and as polymerizing agents for the transesterification reactions with glycols and bisphenols in the production of polycarbonates.

The methods which are most commonly employed for the preparation of the esters in question are based on the reaction between the alcohol and phosgene or chloroformates in the presence of bases, these latter being appropriately selected from among the series of the hydroxides and carbonates of alkali metals and alkaline earth metals, or pyridine and other organic bases. The dangers and the poor industrial adaptability of these methods are such that no doubts are left in this connection. Attempts have been made to skip the known ways, but with poor results. For example, the Japanese Pat. No. 11 129 described the preparation of the carbonate ester by reacting the alcohol concerned with carbon monoxide in the presence of cupric ions: the use of salts of bivalent copper, especially halides, is emphasized in that patent. In this case, the carbonate yields are extremely low and, in addition, the formation of considerable amounts of the alkyl halide, ether and haloid acid is experienced, so that the pH of the solution becomes considerably acidic.

As a whole, it is not possible to envisage a transfer of such a procedure to an industrial scale.

The same Applicants thereof are owners of an Italian Pat. No. 898 077, which relates to a method for the preparation of esters of the carbonic acid, which is based on the reaction between the alcohol, carbon monoxide and oxygen, carried out in the presence of a catalyst system composed by complexes of metals which are capable, by oxy-reduction, of displaying two valency states. The results are no doubt satisfactory, but the use of complexes is affected by a few defects, especially if viewed with the prospect of transfer on an industrial scale. Quite apart from the higher cost of the complex catalyst systems, these generally exhibit a certain sensitivity to the action of water and carbon dioxide which are formed together with the carbonate in the course of the reaction, a fact which imposes a low conversion of the alcohol. There are difficulties, moreover, in the separation of the reaction products and more particularly of water and carbonate from the reactor effluent and from the homogeneous catalyst inasmuch as the ligand is normally an organic base and brings about a certain hydrolysis of the ester due to the water which is present in the system.

We have now found that the same reaction is feasible, under certain conditions, in the presence of simple metal salts, and this fact is most surprising since it was known heretofore that, with such a catalyst system, only polyfunctional alcohols were capable of reacting to give esters at the carbonic acid (see the Italian Pat. No. 926 748).

The subject-matter of the present invention is a method for the preparation of esters of the carbonic acid comprising the step, as outlined above, of reacting the alcohol concerned with carbon monoxide and oxygen in the presence of a salt of a metal belonging to the Groups, IB, IIB and VIII of the Periodic Table with its metal ion bound to the least possible number of inorganic anions. The use of copper salts has proven to be particularly advantageous. The reaction pattern can thus be summarized:

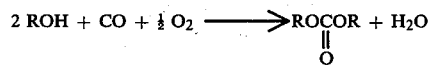

wherein R is a hydrocarbonaceous radical selected among the alkyl, aryl or cycloalkyl radicals: the reaction is carried out by dispersing or dissolving the salt of the metal in question in a solvent which can be the alcohol as itself or another solvent.

The advantage stemming from the use of salts having a restricted number of inorganic anions is considerable, since there is no formation of a high acidity during progress of the reaction. The system remains at pH values of a weakly acidic character during the entire reaction run, so that the reaction itself is not impaired in any way and proceeds to very high carbonate ester yield without experiencing the formation of any appreciable quantities of by-products.

As outlined above, the reaction is carried out either by dispersing or dissolving the metal salt in a solvent medium: through the dispersion or solution thus obtained a stream of CO and $O_2$ is delivered, carbon monoxide and oxygen being fed either separately or admixed together, either continuously or in alternating cycles.

The expected product is separated from the reaction mixture by means of simple physical procedures. In the case of dispersions, for example, filtration is sufficient to remove the catalyst, thus separating the solution which contains the carbonate: the latter shall then be recovered by rectification or crystallization.

The method of the invention can be carried out within a wide range of pressures and temperatures and the top limits are a function, for example, of the stability of the compounds which are employed. Generally speaking, the working temperatures vary from 70° C. to 200° C., the CO and $O_2$ pressures being higher than the atmospherical pressure.

All the working details will be set forth in the ensuing illustrative examples which, however, are not to be construed as limitations of the invention.

EXAMPLE 1

A 200-ml, Teflon-lined autoclave has been charged with 100 mls MeOH and 18 grams of CuBr. The system is oxidized with $O_2$ at 60° C. under a pressure of $O_2$ of 5 atmospheres (gauge) for 90 mins. Subsequently, CO has been fed-in until a pressure of 12 atmospheres (gauge) has been attained and the temperature has been brought to 80° C. Carbon monoxide is replaced in the system as it is being used up in the reaction so as not to alter the total pressure. The reaction was completed after 30 mins. and the solution analyzed by gas chromatographical analysis. There have been obtained a complete conversion of the cooper and a selectivity of 95% of dimethyl carbonate and the residual copper oxidized the carbon monoxide to carbon dioxide. There have been carried out 4 similar subsequent cycles and only a slight increase of selectivity of $CO_2$ in time was observed. In the fourth cycle the molar ratio $CO_2$/dimethyl carbonate was 1 to 9.

EXAMPLE 2

In the apparatus described in Example 1 there have been charged 100 mls methanol and 20 grams of CuCl and the system has been oxidized with $O_2$ to 80° C. and under 10 atmospheres (gauge) for 60 mins. Subsequently, CO has been fed-in under 30 atmospheres (gauge) constant pressure and the temperature has been raised to 100° C. The reaction lasted as long as 90 minutes. On completion of the reaction the copper was still in a completely reduced form. The dimethyl carbonate yield was 95%, whereas the remaining copper oxidized the CO to $CO_2$. The selectivity relative to methanol was total.

EXAMPLE 3

In the apparatus of Example 1 there have been charged 16.4 grams of $CuClO_4$ and 26 grams of methanol. The system has been oxidized with $O_2$ to 100° C. and under a pressure of 5 atmospheres (gauge) during 20 minutes and reduced with CO under 50 atmospheres (gauge) at 100° C. for 2 hours. On completion of the reaction the copper was in a totally reduced form. The dimethyl carbonate yield was over 95%. The remaining copper oxidized CO to $CO_2$ and the selectivity relative to methanol was total.

EXAMPLE 4

The apparatus of Example 1 was charged with 15 grams of methanol and 10 grams of $CuCl_2$. To the system there have been added 3.9 grams of sodium methylate in 20 grams methanol, to such an extent as to neutralize either of the two chlorine ions bound to the copper. The reaction mixture has been brought to 100° C. and placed under 60 atmosphere (gauge) of CO. After two hours a complete reduction of copper to CuCl was experienced and methyl carbonate was obtained with a yield as high as 90% approx. of theory. There has been noted the formation of small amounts of methyl chloride and dimethyl ether, but at any rate less than 0.02%.

EXAMPLE 5

A 6-liter, ceramic-lined autoclave was charged with 3 liters of methanol and 480 grams of CuCl, the temperature was raised to 70° C. and $O_2$ was introduced under a pressure of 8 atmospheres (gauge) until a complete oxidation of the copper was achieved, that which was completed within an hour approximately. Subsequently, the excess of $O_2$ was vented and CO introduced under a pressure of 15 atmospheres (gauges) the pressure being kept constant. Within 3 hours the conversion of copper was total. The selectivity relative to dimethyl carbonate was over 95%, the remaining copper oxidized CO to $CO_2$. The selectivity relative to methanol was total. In the three subsequent cycles the trend of the reaction was substantially the same as before. Only a slight increase of $CO_2$ between a reaction cycle and the next was observed.

EXAMPLE 6

The apparatus described in Example 5 has been charged with 3 liters of methanol and 480 grams of CuCl, the temperature raised to 100° C. and $O_2$ was fed-in under a pressure of 10 atmospheres (gauge) until a complete oxidation of copper was achieved, that which took about 30 minutes. The excess oxygen was vented and CO was fed-in under a pressure of 20 atmospheres (gauge), the temperature being maintained at 120° C. After 20 mins. the reaction was completed and the selectivity relative to dimethyl carbonate was 92%. The residual copper oxidized CO to $CO_2$.

EXAMPLE 7

The apparatus described in Example 5 was charged with 3 liters of methanol and 480 grams of CuCl. The thermostatically controlled system was fed at 102° C. with 150 normal liters an hour of CO and 50 normal liters an hour of $O_2$ simultaneously under a total pressure of 30 atmospheres (gauge). The system was continually vented by discharging 50 normal liters hourly of a gas mixture which was essentially composed by 97% CO, from 2% to 3% $CO_2$ and from 0.1% to 0.4% $O_2$, after a 4-hour run the conversion of methanol was 30% and the selectivity relative to dimethyl carbonate was 95%.

EXAMPLE 8

The apparatus described in Example 1 was charged with 16 grams $CuSO_4$ and 30 mls methanol: to the system there was added 3.8 grams of lithium methoxide in 10 mls methanol so as to neutralize one half of the sulphate ion. CO was fed-in under 50 atmospheres (gauge) and the temperature was brought to 110° C. After two hours the copper was entirely reduced to $Cu_2SO_4$. Dimethyl carbonate was obtained with a yield of 75% relative to copper: the remaining copper had oxidized CO to $CO_2$. The selectivity relative to methanol was total.

We claim:
1. A method for the preparation of carbonic acid esters of formula $(RCO)_2O$ wherein R is an alkyl or cycloalkyl radical, said method comprising reacting an alcohol of the formula ROH wherein R is as described above, with oxygen and carbon monoxide in the presence of a catalyst consisting of a copper metal salt of the group of cuprous salts and cupric salts having a single inorganic anion.
2. A method for the preparation of dimethyl carbonate wherein methanol is reacted with oxygen and carbon monoxide in the presence of a catalyst consisting of a monovalent copper salt selected from the group of cuprous bromide, copper perchlorate, and cuprous chloride.
3. The method of claim 2 wherein methanol is first contacted with oxygen and then with carbon monoxide.
4. The method of claim 2 wherein methanol is contacted simultaneously with oxygen and carbon monoxide.
5. The method of claim 1 or 2 wherein the reaction is carried out at a temperature in the range of 70° C. to 200° C.
6. The method of claim 1 or 2 wherein the reaction is carried out at a pressure greater than atmospheric pressure.
7. The method of claim 1 or 2 wherein the reaction is carried out in the presence of a solvent medium.

* * * * *